US008927768B2

(12) United States Patent
Boussie et al.

(10) Patent No.: US 8,927,768 B2
(45) Date of Patent: *Jan. 6, 2015

(54) PRODUCTION OF ADIPIC ACID AND DERIVATIVES FROM CARBOHYDRATE-CONTAINING MATERIALS

(71) Applicant: Rennovia, Inc., Menlo Park, CA (US)

(72) Inventors: Thomas R. Boussie, Menlo Park, CA (US); Eric L. Dias, Belmont, CA (US); Zachary M. Fresco, Redwood City, CA (US); Vincent J. Murphy, San Jose, CA (US)

(73) Assignee: Rennovia, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/932,413

(22) Filed: Jul. 1, 2013

(65) Prior Publication Data
US 2014/0024858 A1 Jan. 23, 2014

Related U.S. Application Data

(63) Continuation of application No. 12/814,240, filed on Jun. 11, 2010, now Pat. No. 8,501,989.

(60) Provisional application No. 61/268,414, filed on Jun. 13, 2009.

(51) Int. Cl.
C07C 55/00 (2006.01)
C07C 51/36 (2006.01)
C07C 51/377 (2006.01)
C07C 29/149 (2006.01)
C07C 209/00 (2006.01)
C07C 253/00 (2006.01)
C08G 63/16 (2006.01)
C08G 69/14 (2006.01)
C08G 69/26 (2006.01)

(52) U.S. Cl.
CPC .............. C07C 51/377 (2013.01); C07C 29/149 (2013.01); C07C 209/00 (2013.01); C07C 253/00 (2013.01); C08G 63/16 (2013.01); C08G 69/14 (2013.01); C08G 69/26 (2013.01)
USPC .......................................................... 562/590

(58) Field of Classification Search
None
See application file for complete search history.

(56) References Cited

U.S. PATENT DOCUMENTS

| | | |
|---|---|---|
| 2,472,168 A | 6/1949 | Mehltretter et al. |
| 2,750,394 A | 6/1956 | Peniston |
| 2,851,468 A | 9/1958 | Snyder |
| 2,917,520 A | 12/1959 | Cope |
| 2,929,823 A | 3/1960 | Garber et al. |
| 3,070,633 A | 12/1962 | Utne et al. |
| 3,083,236 A | 3/1963 | Utne et al. |
| 3,118,912 A | 1/1964 | Smith |
| 3,189,651 A | 6/1965 | Garber et al. |
| 3,225,066 A | 12/1965 | Baak |
| 3,326,944 A | 6/1967 | Baak |
| 3,483,228 A | 12/1969 | Garber et al. |
| 3,607,922 A | 9/1971 | Acres et al. |
| 3,671,566 A | 6/1972 | Decker et al. |
| 3,761,579 A | 9/1973 | Curtis, Jr. et al. |
| 3,860,626 A | 1/1975 | Putnin et al. |
| 3,873,614 A | 3/1975 | Lamberti et al. |
| 3,896,056 A | 7/1975 | Benjamin et al. |
| 3,917,707 A | 11/1975 | Williams et al. |
| 4,060,547 A * | 11/1977 | Paulik et al. ............... 562/519 |
| 4,067,900 A | 1/1978 | Intilli |
| 4,078,139 A | 3/1978 | Barton et al. |
| 4,302,432 A | 11/1981 | Polichnowski |
| 4,337,202 A | 6/1982 | Hearon et al. |
| 4,339,387 A | 7/1982 | Fleche et al. |
| 4,363,815 A | 12/1982 | Yu et al. |
| 4,400,468 A * | 8/1983 | Faber ........................ 435/142 |
| 4,401,823 A | 8/1983 | Arena |
| 4,439,551 A | 3/1984 | Yeakey et al. |
| 4,533,743 A | 8/1985 | Medeiros et al. |
| 4,590,283 A | 5/1986 | Gaset et al. |
| 4,605,790 A | 8/1986 | Wojtkowski |

(Continued)

FOREIGN PATENT DOCUMENTS

| | | |
|---|---|---|
| CA | 2097812 A1 | 6/1992 |
| CN | 101486639 | 7/2009 |
| DE | 19609069 A1 | 9/1997 |
| EP | 0096913 A1 | 12/1983 |
| EP | 0151498 A2 | 8/1986 |

(Continued)

OTHER PUBLICATIONS

Database CAPLUS Chemical Abstracts Service, Columbus, Ohio, US; Database Accession No. 1987:477541, Abstract of Bitsi et al., Journal of Organometallic Chemistry (1986).*

(Continued)

Primary Examiner — Karl J Puttlitz
(74) Attorney, Agent, or Firm — Senniger Powers LLP

(57) ABSTRACT

The present invention generally relates to processes for the chemocatalytic conversion of a carbohydrate source to an adipic acid product. The present invention includes processes for the conversion of a carbohydrate source to an adipic acid product via a furanic substrate, such as 2,5-furandicarboxylic acid or derivatives thereof. The present invention also includes processes for producing an adipic acid product comprising the catalytic hydrogenation of a furanic substrate to produce a tetrahydrofuranic substrate and the catalytic hydrodeoxygenation of at least a portion of the tetrahydrofuranic substrate to an adipic acid product. The present invention also includes products produced from adipic acid product and processes for the production thereof from such adipic acid product.

20 Claims, No Drawings

(56) References Cited

U.S. PATENT DOCUMENTS

| | | |
|---|---|---|
| 4,722,997 A | 2/1988 | Roerdink et al. |
| 4,740,605 A | 4/1988 | Rapp |
| 4,767,856 A | 8/1988 | Dockner et al. |
| 4,820,880 A | 4/1989 | Urbas |
| 4,833,230 A | 5/1989 | Kiely et al. |
| 4,843,173 A | 6/1989 | Saito et al. |
| 4,845,208 A | 7/1989 | Fuertes et al. |
| 4,900,407 A | 2/1990 | Saito et al. |
| 4,912,237 A | 3/1990 | Zeitsch |
| 4,971,657 A | 11/1990 | Avignon et al. |
| 4,977,283 A | 12/1990 | Leupold et al. |
| 5,071,754 A | 12/1991 | Walkup et al. |
| 5,132,452 A | 7/1992 | Deller et al. |
| 5,132,456 A | 7/1992 | King et al. |
| 5,149,680 A | 9/1992 | Kitson et al. |
| 5,196,617 A | 3/1993 | Kovenklioglu et al. |
| 5,247,012 A | 9/1993 | Vyvoda |
| 5,252,473 A | 10/1993 | Walkup et al. |
| 5,264,624 A | 11/1993 | Vogtel et al. |
| 5,276,240 A | 1/1994 | Timmons et al. |
| 5,281,647 A | 1/1994 | Eapen |
| 5,290,852 A | 3/1994 | Vyvoda |
| 5,359,137 A | 10/1994 | Burke |
| 5,426,219 A | 6/1995 | Lehnhardt et al. |
| 5,426,252 A | 6/1995 | Sherif |
| 5,430,214 A | 7/1995 | Smith et al. |
| 5,434,233 A | 7/1995 | Kiely et al. |
| 5,484,914 A | 1/1996 | Skibida et al. |
| 5,487,987 A | 1/1996 | Frost et al. |
| 5,516,960 A | 5/1996 | Robinson |
| 5,562,777 A | 10/1996 | Farone et al. |
| 5,599,977 A | 2/1997 | Kiely et al. |
| 5,616,496 A | 4/1997 | Frost et al. |
| 5,625,110 A | 4/1997 | Schoedel et al. |
| 5,683,952 A | 11/1997 | Onozawa et al. |
| 5,721,189 A | 2/1998 | Zhang |
| 5,726,046 A | 3/1998 | Farone et al. |
| 5,731,467 A | 3/1998 | Fleche |
| 5,766,439 A | 6/1998 | Eyal et al. |
| 5,772,013 A | 6/1998 | Kunz et al. |
| 5,773,677 A | 6/1998 | Lansink-Rotgerink et al. |
| 5,789,333 A | 8/1998 | Angelici et al. |
| 5,811,628 A | 9/1998 | Weber et al. |
| 5,820,687 A | 10/1998 | Farone et al. |
| 5,900,511 A | 5/1999 | Sengupta et al. |
| 5,919,994 A | 7/1999 | Rao |
| 5,922,635 A | 7/1999 | Olah et al. |
| 5,981,420 A | 11/1999 | Nakano et al. |
| 5,986,127 A | 11/1999 | Ionkin et al. |
| 5,998,657 A | 12/1999 | Gogate et al. |
| 6,008,418 A | 12/1999 | Baur et al. |
| 6,028,025 A | 2/2000 | Ying et al. |
| 6,049,004 A | 4/2000 | Kiely et al. |
| 6,087,296 A | 7/2000 | Harper |
| 6,127,585 A | 10/2000 | Duzick et al. |
| 6,147,208 A | 11/2000 | Achhammer et al. |
| 6,180,830 B1 | 1/2001 | Jacquot |
| 6,228,800 B1 | 5/2001 | Yamaguchi et al. |
| 6,232,264 B1 | 5/2001 | Lukehart et al. |
| 6,391,821 B1 | 5/2002 | Satoh et al. |
| 6,403,521 B1 | 6/2002 | Ishii et al. |
| 6,436,866 B1 | 8/2002 | Nishikido et al. |
| 6,441,202 B1 | 8/2002 | Lightner |
| 6,444,608 B1 | 9/2002 | Oki et al. |
| 6,462,220 B1 | 10/2002 | Luyken et al. |
| 6,476,260 B1 | 11/2002 | Herrmann et al. |
| 6,495,730 B1 | 12/2002 | Konishi et al. |
| 6,498,269 B1 | 12/2002 | Merbouh et al. |
| 6,500,649 B2 | 12/2002 | Fouache et al. |
| 6,518,440 B2 | 2/2003 | Lightner |
| 6,521,779 B1 | 2/2003 | Boschat et al. |
| 6,559,275 B2 | 5/2003 | Minami et al. |
| 6,569,670 B2 | 5/2003 | Anderson et al. |
| 6,569,802 B1 | 5/2003 | Ionkin |
| 6,692,578 B2 | 2/2004 | Schmidt et al. |
| 6,716,339 B2 | 4/2004 | Liu et al. |
| 6,743,928 B1 | 6/2004 | Zeitsch |
| 6,773,512 B2 | 8/2004 | Ennelin et al. |
| 6,894,135 B2 | 5/2005 | Kiely et al. |
| 6,894,160 B2 | 5/2005 | Capan et al. |
| 6,897,338 B2 | 5/2005 | Zhong et al. |
| 6,953,873 B2 | 10/2005 | Cortright et al. |
| 6,958,405 B2 | 10/2005 | Le-Khac et al. |
| 7,084,090 B2 | 8/2006 | Ishii et al. |
| 7,115,541 B2 | 10/2006 | Ishii et al. |
| 7,138,035 B2 | 11/2006 | Cui et al. |
| 7,161,005 B2 | 1/2007 | Schlingloff et al. |
| 7,166,743 B2 | 1/2007 | Zhong et al. |
| 7,179,366 B2 | 2/2007 | Harle et al. |
| 7,317,116 B2 | 1/2008 | Sanborn |
| 7,344,696 B2 | 3/2008 | Canos et al. |
| 7,354,743 B2 | 4/2008 | Vlasenko et al. |
| 7,364,880 B2 | 4/2008 | Ray et al. |
| 7,371,894 B2 | 5/2008 | Wonders et al. |
| 7,385,081 B1 | 6/2008 | Gong |
| 7,393,676 B2 | 7/2008 | Gokarn et al. |
| 7,399,855 B2 | 7/2008 | Frost |
| 7,411,078 B2 | 8/2008 | Miura et al. |
| 7,432,382 B2 | 10/2008 | Sanborn et al. |
| 7,459,597 B2 | 12/2008 | Koivusalmi et al. |
| 7,517,675 B2 | 4/2009 | Vercauteren et al. |
| 7,572,925 B2 | 8/2009 | Dumesic et al. |
| 7,579,489 B2 | 8/2009 | Sanborn |
| 7,579,490 B2 | 8/2009 | Sanborn et al. |
| 7,582,444 B2 | 9/2009 | Hughes |
| 7,608,689 B2 | 10/2009 | Harris et al. |
| 2002/0111458 A1 | 8/2002 | Minami et al. |
| 2003/0015457 A1 | 1/2003 | Liu et al. |
| 2005/0009694 A1 | 1/2005 | Watts et al. |
| 2005/0233423 A1 | 10/2005 | Berka et al. |
| 2005/0272134 A1 | 12/2005 | Hughes |
| 2006/0084800 A1 | 4/2006 | Chenault |
| 2006/0084817 A1 | 4/2006 | Chenault |
| 2007/0027341 A1 | 2/2007 | Rossi et al. |
| 2007/0031918 A1 | 2/2007 | Dunson, Jr. et al. |
| 2007/0031919 A1 | 2/2007 | Dunson, Jr. et al. |
| 2007/0111294 A1 | 5/2007 | Burgard et al. |
| 2007/0166220 A1 | 7/2007 | Ceyer et al. |
| 2007/0193960 A1 | 8/2007 | Frank et al. |
| 2007/0215484 A1 | 9/2007 | Peterson et al. |
| 2007/0219397 A1 | 9/2007 | Holladay et al. |
| 2007/0287845 A1 | 12/2007 | Lilga et al. |
| 2008/0033187 A1 | 2/2008 | Zhao et al. |
| 2008/0033188 A1 | 2/2008 | Dumesic et al. |
| 2008/0033205 A1 | 2/2008 | Kiely et al. |
| 2008/0041366 A1 | 2/2008 | Wahnon |
| 2008/0096242 A1 | 4/2008 | Sanders et al. |
| 2008/0103232 A1 | 5/2008 | Lake et al. |
| 2008/0103318 A1 | 5/2008 | Lilga et al. |
| 2008/0103340 A1 | 5/2008 | Binder et al. |
| 2008/0206562 A1 | 8/2008 | Stucky et al. |
| 2008/0216391 A1 | 9/2008 | Cortright et al. |
| 2008/0293109 A1 | 11/2008 | Berka et al. |
| 2008/0300434 A1 | 12/2008 | Cortright et al. |
| 2008/0300435 A1 | 12/2008 | Cortright et al. |
| 2009/0018300 A1 | 1/2009 | Bloom et al. |
| 2009/0047719 A1 | 2/2009 | Burgard et al. |
| 2009/0131259 A1 | 5/2009 | Kiely et al. |
| 2009/0171037 A1 | 7/2009 | Aoshima et al. |
| 2009/0211942 A1 | 8/2009 | Cortright et al. |
| 2009/0215128 A1 | 8/2009 | Vlasenko et al. |
| 2009/0250653 A1 | 10/2009 | Kiely et al. |
| 2009/0255171 A1 | 10/2009 | Dumesic et al. |
| 2009/0270245 A1 | 10/2009 | Kumar et al. |
| 2009/0305364 A1 | 12/2009 | Burgard et al. |
| 2010/0113263 A1 | 5/2010 | Lee et al. |

FOREIGN PATENT DOCUMENTS

| | | |
|---|---|---|
| EP | 1728844 A1 | 12/2006 |
| EP | 2033958 A1 | 3/2009 |
| FR | 2556344 A1 | 6/1985 |
| FR | 2663933 A1 | 1/1992 |
| FR | 2664273 A1 | 1/1992 |

(56) References Cited

FOREIGN PATENT DOCUMENTS

| | | |
|---|---|---|
| FR | 2669635 A1 | 5/1992 |
| GB | 591858 | 9/1947 |
| GB | 600871 | 4/1948 |
| GB | 876463 | 9/1961 |
| GB | 1044883 | 10/1966 |
| JP | 33-7620 | 8/1958 |
| JP | 53-144506 | 12/1978 |
| JP | 55-013243 | 1/1980 |
| JP | 59-190984 | 10/1984 |
| JP | 2-088569 A | 3/1990 |
| JP | 2001-316311 A | 11/2001 |
| JP | 2002-308819 A | 10/2002 |
| JP | 2005-060447 A | 3/2005 |
| JP | 2005-200321 | 7/2005 |
| JP | 2005-232116 A | 9/2005 |
| JP | 2007-145736 A | 6/2007 |
| LV | 10857 B | 8/1996 |
| WO | 8201701 A1 | 5/1982 |
| WO | 9421690 A2 | 9/1994 |
| WO | 9507996 A1 | 3/1995 |
| WO | 9604224 A1 | 2/1996 |
| WO | 9638402 A1 | 12/1996 |
| WO | 2005003072 A1 | 1/2005 |
| WO | 2006005070 A1 | 1/2006 |
| WO | 2006100584 A2 | 9/2006 |
| WO | 2006119357 A2 | 11/2006 |
| WO | 2007075370 A2 | 7/2007 |
| WO | 2007075476 A2 | 7/2007 |
| WO | 2007089677 A2 | 8/2007 |
| WO | 2007141293 A1 | 12/2007 |
| WO | 2008021054 A2 | 2/2008 |
| WO | 2008070762 A1 | 6/2008 |
| WO | 2008109877 A1 | 9/2008 |
| WO | 2008144514 A2 | 11/2008 |

OTHER PUBLICATIONS

Abbadi, A., et al., "Effect of pH in the Pt-Catalyzed Oxidation of D-Glucose to D-Gluconic Acid," 1995, J. Mol. Catal. A: Chem., 97:111-118.

Abbadi, A., et al., "Highly Selective Oxidation of Aldonic Acids to 2-Keto-Aldonic Acids Over Pt-Bi and Pt-Pb Catalysts," 1995, App. Catal. A: General, 124:409-417.

Blanc, B., et al., "Starch-Derived Polyols for Polymer Technologies: Preparation by Hydrogenolysis on Metal Catalysts," Apr. 2000, Green Chemistry, pp. 89-91.

Brown, J.M., Equilibration of D-Glucaric Acid in Aqueous Solution, 2007, Thesis, University of Waikato, 191 pages.

Dirkx, J., et al., "The Oxidation of Glucose with Platinum on Carbon as Catalyst," 1981, J. Catal., 67:1-13.

Dirkx, J., et al., "The Oxidation of Gluconic Acid with Platinum on Carbon as Catalyst," 1981, J. Catal., 67:14-20.

Gehret, T. et al., "Convenient Large-Scale Synthesis of D-Glucaro-1,4:6,3-dilactone," 2009, J. Org. Chem., 74 (21), pp. 8373-8376.

Koso, S., et al., "Chemoselective Hydrogenolysis of Tetrahydrofurfuryl Alcohol to 1,5-Pentanediol," 2009, Chem. Commun., 2035-2037.

Koso, S., et al., "Promoting Effect of Mo on the Hydrogenolysis of Tetrahydrofurfuryl Alcohol to 1,5-pentanediol Over Rh/SiO2," 2009, J. Catal., 267:89-92.

Abstract of BG 100407, Episucres SA, 1997, 1 page.

Saha, B.C., "Hemicellulose Bioconversion," J. Ind. Microbiol. Biotechnol., 2003, 30:279-291.

Venema, F., et al., "Platinum-Catalyzed Oxidation of Aldopentoses to Aldaric Acids," 1992, J. Mol. Catal., 77:75-85.

Wang, T., et al., "Aqueous-Phase Aerobic Oxidation of Alcohols by Soluble Pt Nanoclusters in the Absence of Base," 2007, Chem. Commun., 4375-4377.

Wang T., et al., "Base-free Aqueous-Phase Oxidation of Non-Activated Alcohols with Molecular Oxygen on Soluble Pt Nanoparticles," 2009, Green Chem, 11:562-568.

Besson, M., et al., "Oxidation of Glucose and Gluconate on Pt, Pt Bi, and Pt Au Catalysts," 1996, Recueil des Travaux chimiques des pays-Bas, 115:217-221.

De La Motte, H., "Ueber die Einwirkung von Phosphorpentachlorid und Jodwasserstoffsaure auf Zuckersaure," 1879, Berichte Der Deutschen Chemischen Gesellschaft, 12/2:1571-1573.

Fischer, E., et al., "Ueber eine neue Pentonsaure und die zweite inactive Trioxyglutarsaure," 1891, Berichte Der Deutschen Chemischen Gesellschaft, 24/2:4216-4225.

Tiemann, F., et al., "Ueber Isozuckersaure," 1886, Berichte Der Deutschen Chemischen Gesellschaft, 19/1:1257-1281.

"Roadmap for Biomass Technologies in the United States," Dec. 2002, U.S. Dept. of Energy, 48 pages.

"Top Value Added for Chemicals from Biomass—vol. 1: Results of Screening for Potential Candidates from Sugars and Synthesis Gas," 2004, Produced by PNNL, NREL and EERE, T. Werpy and G. Petersen, Eds., U.S. Dept. of Energy, 76 pages.

"Acidum Tartaricum (U.S.P.)—Tartaric Acid," 2/42010, Henriette's Herbal Homepage, www.henriettesherbal.com/eclectic/kings/acidum-tart.html, 5 pages.

International Search Report issued in PCT/US2010/038419, dated Jan. 31, 2011, 7 pages.

Written Opinion issued in PCT/US2010/038419, dated Jan. 31, 2011, 14 pages.

International Search Report issued in PCT/US2010/038422, dated Sep. 16, 2010, 6 pages.

Written Opinion issued in PCT/US2010/038422, dated Sep. 16, 2010, 11 pages.

International Search Report issued in PCT/US2010/038408, dated Feb. 2, 2011, 7 pages.

Written Opinion issued in PCT/US2010/038408, dated Feb. 2, 2011, 16 pages.

Casanova, O., et al., "Biomass into Chemicals: Aerobic Oxidation of 5-Hydroxymethyl-2-Furfural into 2,5-Furandicarboxylic Acid with Gold Nanoparticle Catalysts," 2009, ChemSusChem, 2:1138-1144.

Clarke, J.K.A., et al., "Preparation of Supported Platinum-Gold Catalysts and Alkane Reactions on Selected Platinum and Platinum-Gold Supported Clusters," 1984, App Catalysis, 9:85-108.

Dimitratos, N., et al., "Synergetic Effect of Platinum or Palladium on Gold Catalyst in the Selective Oxidation of D-Sorbitol," 2005, Catalysis Letters, 99:3-4:181-185.

Dirkx, J., et al., "The Preparation of D-Glucaric Acid by the Oxidation of D-Gluconic Acid Catalysed by Platinum on Carbon," 1977, Carbohydrate Research, 59:63-72.

Ibert, M., et al., "Determination of the Side-Products Formed During the Nitroxide-Mediated Bleach Oxidation of Glucose to Glucaric Acid," 2002, Carbohydrate Res, 337:1059-1063.

Lewkowski, J., "Synthesis, Chemistry and Applications of 5-Hydroxymethylfurfural and its Derivatives," 2001, Arkivoc (i):17-54.

Mallat, T., et al, "Oxidation of Alcohols with Molecular Oxygen on Solid Catalysts," 2004, Chem Rev, 104:3037-3058.

Mamman, A.S., et al. "Furfural: Hemicellulose/xylose-Derived Biochemical," 2008, Biofuels, Bioprod. Bioref., 2:438-454.

Mehltretter, C.L., et al., "Sugar Oxidation, Saccharic and Oxalic Acids by the Nitric Acid Oxidation of Dextrose," 1953, Ag and Food Chem, 1/12:779-783.

Merbouh, N., et al., "Facile Nitroxide-mediated Oxidations of D-Glucose to D-Glucaric Acid," 2001, Carbohydrate Res, 336:75-78.

Moore, J.A., et al., "An Improved Hydrogenation for the Preparation of Tetrahydrofuran cis-2,5-Dicarboxylic Acid," 1972, Organic Preparations and Procedures Int., 4/6:289-292.

Moreau, C., et al., "Recent Catalytic Advances in the Chemistry of Substituted Furans from Carbohydrates and in the Ensuing Polymers," 2004, Topics in Catalysis, 27/1-4:11-30.

Niu, W., et al., "Benzene-Free Synthesis of Adipic Acid," 2002, Biotechnol Prog, 18:201-211.

Ortiz-Soto, L.B., et al, "Structure-Sensitivity of Propylene Hydrogenation Over Cluster-Derived Bimetallic Pt-Au Catalysts," 2006, Catalysis Letters, 107/1-2:13-17.

Pamuk, V., et al., "The Preparation of D-Glucaric Acid by Oxidation of Molasses in Packed Beds," 2001, J Chem Technol Biotechnol, 76:186-190.

(56) References Cited

OTHER PUBLICATIONS

Prati, L., et al., "Effect of Gold Addition on Pt and Pd Catalysts in Liquid Phase Oxidations," 2007, Topics in Catalysis, 44/1-2:319-324.

Röper, H., "Selective Oxidation of D-Glucose: Chiral Intermediates for Industrial Utilization," 1991, Carbohydrates As Organic Raw Materials, F.W. Lichtenhaler (Ed), Verlag Chemie, Weinheim, Germany, pp. 267-288.

Shen, Y., et al., "Efficient Synthesis of Lactic Acid by Aerobic Oxidation of Glycerol on Au-Pt/TiO2 Catalysts," 2010, Chem Eur J, 16:7368-7371.

Smits, P.C.C., et al., "The Selective Oxidation of Aldoses and Aldonic Acids to 2-Ketoaldonic Acids with Lead-Modified Platinum-on-Carbon Catalysts," 1986, Carbohydrate Res, 153:227-235.

Smits, P.C.C., et al., "Lead Modified Platinum on Carbon Caralysts for the Selective Oxidation of (2-) Hydroxycarbonic Acids, and Especially Polyhydroxycarbonic Acids to Their 2-Keto Derivatives," 1987, App Catalysis, 33:83-96.

Thaburet, J-F., et al., "TEMPO-mediated Oxidation of Maltodextrins and D-Glucose: Effect of pH on the Selectivity and Sequestering Ability of the Resulting Polycarboxylates," 2001, Carbohydrate Res, 330:21-29.

Wenkin, M., et al., "Influence of Metallic Precursors on the Properties of Carbon-Supported Bismuth-Promoted Palladium Catalysts for the Selective Oxidation of Glucose to Gluconic Acid," 1996, App Catalysis A: General, 148:181-199.

Kouremenos, K.A., et al., Metabolic Profiling of Infant Urine Using Comprehensive Two-Dimensional Gas Chromatography: Application to the Diagnosis of Organic Acidurias and Biomarker Discovery, 2010, J Chromotography A, 1217:104-111.

Dijkgraaf, P.J.M., "Oxidation of Glucose to Glucaric Acid by Pt/C Catalysts," 1989, 105 pages, Thesis, Technische Universiteit Eindhoven.

Lichtenthaler, F.W., et al., "Carbohydrates as Green Raw Materials for the Chemical Industry," 2004 C.R. Chimie 7:65-90.

Merbouh, N., et al., "4-AcNH-TEMPO-Catalyzed Oxidation of Aldoses to Aldaric Acids Using Chlorine or Bromine as Terminal Oxidants," 2002, J Carbohydrate Chem, 21/1&2: 65-77.

International Search Report issued in PCT/US2010/060143 dated Apr. 5, 2011, 6 pages.

Written Opinion issued in PCT/US2010/060143 dated Apr. 5, 2011, 9 pages.

Scifinder Search Results on "Xylaric Acid"—search conducted on Mar. 15, 2010, 11 Pages.

Gao, S., et al., "Low-Molecular-Weight and Oligomeric Components in Secondary Organic Aerosol from the Ozonolysis of Cycloalkenes and $\alpha$-Pinene," 2004, J Phys Chem A, 108:10147-10164.

Guneral, F., et al., "Age-Related Reference Values for Urinary Organic Acids in a Healthy Turkish Pediatric Population," 1994, Clin Chem, 40(6):862-868.

Pankow, J.F., et al., "Modeling the Formation of Secondary Organic Aerosol. 1. Application of Theoretical Principles to Measurements Obtained in the $\alpha$-Pinene/, $\beta$-Pinene/, Sabinene/, $\Delta$-Carene/, and Cyclohexene/Ozone Systems," 2001, Environ Sci Technol, 35:1164-1172.

Yang, L., et al., "Photooxidation of Dicarboxylic Acids-Part II: Kinetics, Intermediates and Field Observations," 2008, Atmospheric Environment, 42:868-880.

"Adipic Acid," compounds 24,052-4 and A2,635-7 in Aldrich Handbook of Fine Chemicals and Laboratory Equipment, Nederlands Edition, 2000, p. 40, Sigma-Aldrich, USA.

International Search Report issued in PCT/US2010/060147 dated Apr. 29, 2011, 4 pages.

Written Opinion issued in PCT/US2010/060147 dated Apr. 29, 2011, 10 pages.

Habrioux, A., et al., "Activity of Platinum-Gold Alloys for Glucose Electrooxidation in Biofuel Cells," 2007, J Phys Chem B, 111:10329-10333.

Kerzenmacher, S., et al., "Energy Harvesting by Implantable Abiotically Catalyzed Glucose Fuel Cells," 2008, J Power Sources, 182:1-17.

Second Written Opinion issued in PCT/US2010/060143 dated May 30, 2012, 6 pages.

Database CAPLUS Chemical Abstracts Service, Columbus, Ohio, US; Database Accession No. 1987:477541, Abstract of Bitsi et al., Journal of Organometallic Chemistry (1986), 310(1), 115-19.

White, et al., Basic Energy Sciences Advisory Committee Subpanel Workshop Report, Opportunities for Catalysis in the 21st Century, 2002, pp. 1-47.

Satoh, S., et al., "Electrochemical Reductive Cyclization of Dimethyl Dibromoalkanedioates," 1980, Hok Kaido Dai gaku Kogakubu KenKyu Hokoku, 102:33.

Yong, G., et al., "Efficient Catalytic System for the Selective Production of 5-Hydroxymethylfurfural from Glucose and Fructose," 2008, Angew Chem Int Ed, 47:9345-9348.

\* cited by examiner

US 8,927,768 B2

PRODUCTION OF ADIPIC ACID AND DERIVATIVES FROM CARBOHYDRATE-CONTAINING MATERIALS

REFERENCE TO RELATED APPLICATIONS

This application is a continuation of U.S. patent application Ser. No. 12/814,240, filed Jun. 11, 2010, now U.S. Pat. No. 8,501,989, issued Aug. 6, 2013, and claims benefit of U.S. provisional application Ser. No. 61/268,414, filed Jun. 13, 2009, the entire disclosures of which are incorporated herein by reference.

FIELD OF THE INVENTION

The present invention generally relates to processes for the chemocatalytic conversion of a carbohydrate source to an adipic acid product. The present invention includes processes for the conversion of a carbohydrate source to an adipic acid product via a furanic substrate, such as 2,5-furandicarboxylic acid or derivatives thereof. The present invention also includes processes for producing an adipic acid product comprising the catalytic hydrogenation of a furanic substrate to produce a tetrahydrofuranic substrate and the catalytic hydrodeoxygenation of at least a portion of the tetrahydrofuranic substrate to an adipic acid product. The present invention also relates to processes for the preparation of industrial chemicals such as adiponitrile, hexamethylene diamine, caprolactam, caprolactone, adipate esters, 1,6-hexanediol, polyamides (e.g., nylons) and polyesters from an adipic acid product obtained from processes including the catalytic hydrodeoxygenation of a tetrahydrofuranic substrate. The invention is further directed to such industrial chemicals produced from adipic acid product produced by the processes of the present invention.

BACKGROUND OF THE INVENTION

For at least the last forty years, experts in the scientific and economic communities have been predicting diminishing availability of petrochemical resources to produce the energy and chemical-based materials needed throughout the world. Fortunately, for much of this period, newly discovered petroleum reserves, and advances in petroleum production and conversion technologies have enabled the supply of these resources and the products producible therefrom to substantially keep pace with the ever-increasing demands. More recently, however, the rapid rate of industrialization of the world's most populous countries, China and India, coupled with increased political instability in petroleum-producing regions (most notably the Middle East, Nigeria, and Venezuela), have pushed oil prices to record levels, adversely affecting the US economy, among others. Moreover, environmental, ecological, and political considerations in the US continue to impact the production of this valuable resource by, among other matters, removing proven reserves from commercial exploitation.

The combined effects of ever-increasing demand and slowing rates of increase in the production of petroleum affect not only gasoline, diesel fuel and heating oil prices but also the prices of the vast array of chemicals that are feedstock's for an equally vast array of products, from drugs to plastics to pesticides, to name a few.

Over the past decade, this adverse economic impact has become a driving factor for developing alternative and sustainable ways to meet chemical-based materials needs. The Roadmap for Biomass Technologies in the United States (U.S. Department of Energy, Accession No. ADA436527, December 2002), authored by 26 leading experts, predicts that, by 2030, 25% of all chemicals consumed in the United States will be produced from biomass. More recently, the U.S. Department of Energy has identified 12 top-tier chemical building blocks from biomass processing, as reported in the Biomass Report for the DOE Office of Energy Efficiency and Renewable Energy entitled Top Value Added Chemicals from Biomass, Volume 1-Results of Screening for Potential Candidates from Sugars and Synthesis Gas, August 2004.

It has been reported that of the approximately 200 billion tons of biomass produced per year, 95% of it is in the form of carbohydrates, and only 3 to 4% of the total carbohydrates are currently being used for food and other purposes. Thus, there is an abundant untapped supply of biomass carbohydrates, which can potentially be used for the production of non-petroleum based specialty and industrial chemicals that are fully renewable. That said, biorenewable routes to sustainable supplies of valuable chemicals such as, for example, alcohols, aldehydes, ketones, carboxylic acids, and esters useful for producing a vast array of products are less likely to become a reality until the cost of converting biomass to these chemicals is more nearly comparable to or, more preferably, advantaged as compared to the corresponding production cost from petroleum-based feedstocks.

Adipic acid is among the end products producible from biorenewable feedstocks. Such processes have been disclosed in, for example, U.S. Pat. Nos. 4,400,468 and 5,487,987 and, for example, in "Benzene-Free Synthesis of Adipic Acid", Frost et al. Biotechnol. Prog. 2002, Vol. 18, pp. 201-211. However, to date, no process for producing adipic acid from biorenewable feedstocks has been commercialized.

Among the list of 12 building block chemicals targeted by the US government for production from biomass is 2,5-furandicarboxylic acid, and the government has solicited proposals for the use thereof in the production of industrial chemicals. To date, large scale production of high value industrial chemicals from 2,5-furandicarboxylic acid has not been achieved.

To that end, applicants have discovered processes which enable the production of high value, large market industrial chemicals cost effectively from a key building block material such as 2,5-furandicarboxylic acid.

SUMMARY OF THE INVENTION

Briefly, therefore, the present invention is directed to processes for preparing an adipic acid product from a carbohydrate source comprising the steps of converting the carbohydrate source to a furanic substrate and converting at least a portion of the furanic substrate to the adipic acid product. In accordance with various embodiments, processes for producing an adipic acid product from a furanic substrate are disclosed which comprise converting by chemocatalytic means at least a portion of the furanic substrate to the adipic acid product. Further, in accordance with the present invention, processes for producing an adipic acid product further comprise converting at least a portion of the furanic substrate to a tetrahydrofuranic substrate and converting at least a portion of the tetrahydrofuranic substrate to the adipic acid product.

In accordance with various embodiments, the process for preparing an adipic acid product comprises converting by chemocatalytic means to the adipic acid product a substrate of formula I

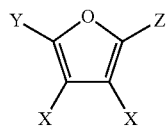

or a salt thereof, or an intermolecular homomer or heteromer thereof, or intermolecular or intramolecular anhydrides or stereoisomers thereof, all collectively referred to as "furanic substrate," wherein each X is independently selected from the group consisting of —OH, —OR$^2$, and —H, or, in some embodiments, X is independently selected from the group consisting of —OH and —H, or, in some embodiments, each X is —OH, or, in some embodiments, each X is —H; Y is selected from the group consisting of —C(O)OH, —C(O)OR$^1$, —C(O)NR$^3$R$^4$, and —CH$_2$NR$^3$R$^4$; Z is selected from the group consisting of —C(O)OH, —C(O)OR$^1$, —C(O)NR$^3$R$^4$, and —CH$_2$NR$^3$R$^4$; each R$^1$ is independently selected from the group consisting of hydrocarbyl and substituted hydrocarbyl; each R$^2$ is independently selected from the group consisting of hydrocarbyl and substituted hydrocarbyl; each R$^3$ is independently selected from the group consisting of hydrogen, hydrocarbyl, and substituted hydrocarbyl; each R$^4$ is independently selected from the group consisting of hydrogen, hydrocarbyl, and substituted hydrocarbyl; and, preferably, each hydrocarbyl or substituted hydrocarbyl in any of the aforementioned R$^1$, R$^2$, R$^3$, and/or R$^4$ can be independently selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl and heteroarylalkyl, in each case optionally substituted.

In various embodiments, the present invention is directed to processes for preparing an adipic acid product comprising reacting a tetrahydrofuranic substrate with hydrogen, in the presence of a hydrodeoxygenation catalyst, a solvent and a source of halogen, to convert at least a portion of the tetrahydrofuranic substrate to the adipic acid product, wherein the tetrahydrofuranic substrate is a compound of formula III (and salts thereof),

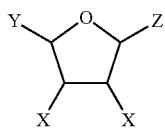

wherein each X is independently selected from the group consisting of —OH, —OR$^2$, and —H, or, in some embodiments, X is independently selected from the group consisting of —OH and —H, or, in some embodiments, each X is —OH, or, in some embodiments, each X is —H; Y is selected from the group consisting of —C(O)OH, —C(O)OR$^1$, —C(O)NR$^3$R$^4$, and —CH$_2$NR$^3$R$^4$; Z is selected from the group consisting of —C(O)OH, —C(O)OR$^1$, —C(O)NR$^3$R$^4$, and —CH$_2$NR$^3$R$^4$; each R$^1$ is independently selected from the group consisting of hydrocarbyl, and substituted hydrocarbyl; each R$^2$ is independently selected from the group consisting of hydrocarbyl and substituted hydrocarbyl; each R$^3$ is independently selected from the group consisting of hydrogen, hydrocarbyl, and substituted hydrocarbyl; each R$^4$ is independently selected from the group consisting of hydrogen, hydrocarbyl, and substituted hydrocarbyl; and, preferably, each hydrocarbyl or substituted hydrocarbyl in any of the aforementioned R$^1$, R$^2$, R$^3$, and/or R$^4$ can be independently selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl and heteroarylalkyl, in each case optionally substituted.

The present invention is further directed to processes for preparing adipic acid or derivative thereof by reacting a tetrahydrofuranic substrate comprising tetrahydrofuran-2,5-dicarboxylic acid (THFDCA) with hydrogen in the presence of hydrogen iodide or hydrogen bromide and a solvent, wherein at least a portion of the tetrahydrofuran-2,5-dicarboxylic acid is converted to adipic acid or derivative thereof.

The present invention is further directed to processes for preparing adipic acid or derivative thereof comprising reacting a furanic substrate with hydrogen, in the presence of a hydrogenation catalyst and a solvent, but in the absence of an added source of halogen, to convert at least a portion thereof to a tetrahydrofuranic substrate, and reacting at least a portion of the tetrahydrofuranic substrate with hydrogen, in the presence of a hydrodeoxygenation catalyst, a solvent and an added source of halogen, to convert at least a portion of the tetrahydrofuranic substrate to adipic acid or derivative thereof.

In various embodiments of the present invention, processes for preparing adipic acid product comprise reacting a furanic substrate with hydrogen, in the presence of a hydrogenation catalyst and acetic acid, but in the absence of an added source of halogen, to convert at least a portion thereof to a tetrahydrofuran-2,5-dicarboxylic acid and reacting at least a portion of the tetrahydrofuran-2,5-dicarboxylic acid with hydrogen, in the presence of a hydrodeoxygenation catalyst, solvent and hydrogen iodide or hydrogen bromide, to convert at least a portion of the tetrahydrofuran-2,5-dicarboxylic acid to an adipic acid product comprising adipic acid.

The present invention is further directed to processes for the preparation of industrial chemicals such as adiponitrile, hexamethylene diamine, caprolactam, caprolactone, adipate esters, 1,6-hexanediol, polyamides (e.g., nylons) and polyesters from an adipic acid product obtained from processes for the chemocatalytic conversion of a carbohydrate source, which processes typically include the catalytic hydrodeoxygenation of a tetrahydrofuranic substrate.

The present invention is further directed to processes for the preparation of industrial chemicals such as adiponitrile, hexamethylene diamine, caprolactam, caprolactone, 1,6-hexanediol and polyamides (e.g., nylons) from an adipic acid product obtained from processes for the chemocatalytic conversion of a carbohydrate source, which processes include the catalytic hydrogenation of a furanic substrate and the catalytic hydrodeoxygenation of a tetrahydrofuranic substrate.

The present invention is further directed to adipic acid product, polyamides, polyesters and caprolactam produced at least in part from adipic acid product produced by processes comprising the chemocatalytic conversion of a tetrahydrofuranic substrate, and, more particularly, a tetrahydrofuranic substrate comprising tetrahydrofuran-2,5-dicarboxylic acid or derivative thereof into an adipic acid product.

The present invention is further directed to adipic acid product, polyamides, polyesters and caprolactam produced at least in part from adipic acid product produced by processes comprising the catalytic hydrogenation of a furanic substrate and the catalytic hydrodeoxygenation of a tetrahydrofuranic substrate.

Other objects and features will become apparent and/or will be pointed out hereinafter.

DESCRIPTION OF THE PREFERRED EMBODIMENTS

I. Source Materials

Biorenewable sources such as corn grain (maize), sugar beet, sugar cane as well as energy crops, plant biomass, agricultural wastes, forestry residues, sugar processing residues, plant-derived household wastes, municipal waste, spent paper, switch grass, miscanthus, cassava, trees (hardwood and softwood), vegetation, crop residues (e.g., bagasse and corn stover) are all rich in hexoses, which can be used to produce furan derivatives, such as 5-hydroxymethylfurfural (HMF). Hexoses are readily produced from such carbohydrate sources by hydrolysis. It is also generally known that biomass carbohydrates can be enzymatically converted to glucose, fructose and other sugars. Dehydration of fructose can readily produce furan derivatives such as HMF. Acid hydrolysis of glucose is also known to produce HMF; see, for example, U.S. Pat. No. 6,518,440. Various other methods have been developed for producing HMF including, for example, those described in U.S. Pat. No. 4,533,743 (to Medeiros et al.), U.S. Pat. No. 4,912,237 (to Zeitsch), U.S. Pat. No. 4,971,657 (to Avignon et al.), U.S. Pat. No. 6,743,928 (to Zeitsch), U.S. Pat. No. 2,750,394 (to Peniston), U.S. Pat. No. 2,917,520 (to Cope); U.S. Pat. No. 2,929,823 (to Garber), U.S. Pat. No. 3,118,912 (to Smith), U.S. Pat. No. 4,339,387 (to Fleche et al.), U.S. Pat. No. 4,590,283 (to Gaset et al.), and U.S. Pat. No. 4,740,605 (to Rapp). In the foreign patent literature, see GB 591,858, GB 600,871; and GB 876,463, all of which were published in English. See also, FR 2,663,933, FR 2,664,273, FR 2,669,635, and CA 2,097,812, all of which were published in French. Thus, a variety of carbohydrate sources can be used to produce HMF by a variety of known techniques.

HMF can be converted to 2,5-furandicarboxylic acid (FDCA) by selective oxidation. Examples of processes for the production of FDCA from HMF are disclosed in, for example, U.S. Pat. Nos. 3,326,944 and 4,977,283, U.S. Pat. App. 2008/0103318, and Japanese Laid-open Application No. H02-088569. See also, Corma et al., ChemSusChem., 2009, p 1138. Derivatives of FDCA can also be produced from HMF by processes such as those illustrated in Moreau, Topics in Catalysis 2004, Vol. 27, pp. 11; Lewkowski, Arkivoc, 2001 (i), p. 17; Lichtenthaler, C. R., Chimie, Vol. 7, p. 65; Moore, Organic Preparations and Procedures International, Vol. 4, 1972, p. 289; and also in U.S. Pat. Nos. 3,225,066, 7,579,490 and 7,432,382.

Thus, it is known in the art to produce from carbohydrates a variety of furans and derivatives thereof which applicants have discovered are useful to produce adipic acid product by the processes of the present invention.

II. Furanic Substrate and Hydrogenation Thereof

Applicants have discovered that an adipic acid product of formula II, below, can be produced from a carbohydrate source by processes which comprise converting by chemocatalytic means a substrate of formula I, below, or a salt thereof, or an intermolecular homomer or heteromer thereof, or intermolecular and intramolecular anhydrides or stereoisomers thereof, hereinafter all collectively referred to as "furanic substrate", derivable by means known in the art, in accordance with the following overall reaction

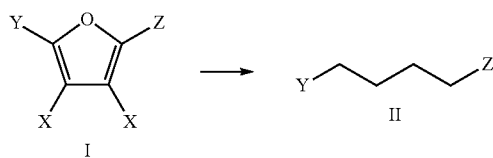

wherein each X is independently selected from the group consisting of —OH, —OR$^2$, and —H or, in some embodiments, X is independently selected from the group consisting of —OH and —H, or in some embodiments, each X is —OH, or, in some embodiments, each X is —H; Y is selected from the group consisting of —C(O)OH, —C(O)OR$^1$, —C(O)NR$^3$R$^4$, and —CH$_2$NR$^3$R$^4$; Z is selected from the group consisting of —C(O)OH, —C(O)OR$^1$, —C(O)NR$^3$R$^4$, and —CH$_2$NR$^3$R$^4$; each R$^1$ is independently selected from the group consisting of hydrocarbyl, and substituted hydrocarbyl; each R$^2$ is independently selected from the group consisting of hydrocarbyl and substituted hydrocarbyl; each R$^3$ is independently selected from the group consisting of hydrogen, hydrocarbyl, and substituted hydrocarbyl; each R$^4$ is independently selected from the group consisting of hydrogen, hydrocarbyl, and substituted hydrocarbyl; and, preferably, each hydrocarbyl or substituted hydrocarbyl in any of the aforementioned R$^1$, R$^2$, R$^3$, and/or R$^4$ can be independently selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl and heteroarylalkyl, in each case optionally substituted. If substituted, the aforementioned R$^1$, R$^2$, R$^3$, and/or R$^4$ can be preferably substituted with one or more of C$_1$-C$_4$ alkyl, hydroxyl, amine, C$_1$-C$_4$ alkylamino, thiol, and C$_1$-C$_4$ thioalkyl.

In accordance with the present invention, the furanic substrate is initially reacted with hydrogen in the presence of a hydrogenation catalyst to convert at least a portion of the furanic substrate to a tetrahydrofuranic substrate, and at least a portion of the tetrahydrofuranic substrate is converted to adipic acid product.

The hydrogenation reaction is typically conducted under conditions known in the art. See for example, "Catalytic Hydrogenation and Dehydrogenation" in *Fine Chemicals Through Heterogeneous Catalysis,* 2nd ed., Sheldon and van Bekkum, p. 351; See also Handbook of Heterogeneous Catalytic Hydrogenation for Organic Synthesis, Nishimura 2001 Wiley, New York. For example, the hydrogenation reaction is conducted in the presence of a solvent to the furanic substrate. Solvents suitable for the hydrogenation reaction include water, alcohols, esters, ethers, ketones, weak carboxylic acids and mixtures thereof. The term "weak carboxylic acid" as used herein means any unsubstituted or substituted carboxylic acid having a pKa of at least about 3.5, more preferably at least about 4.5 and, more particularly, is selected from among unsubstituted acids such as acetic acid, propionic acid or butyric acid, or mixtures thereof. Among the useful solvents, acetic acid is more preferred because it also is useful as a solvent in the subsequent hydrodeoxygenation of the tetrahydrofuranic substrate.

Generally, the temperature of the hydrogenation reaction is at least about 30° C., more typically 60° C., or higher. In various embodiments, the temperature of the hydrogenation reaction is from about 60° C. to about 200° C., and more preferably from about 60° C. to about 160° C.

Typically, the partial pressure of hydrogen is at least about 50 pounds per square inch absolute (psia) (345 kPa), at least about 100 psia (689 kPa), at least about 250 psia (1724 kPa), or at least about 500 psia (3447 kPa). In various embodiments, the partial pressure of hydrogen is up to about 2000 psia (13790 kPa), or more typically in the range of from about 500 psia (3447 kPa) to about 2000 psia (13790 kPa) and still more typically in the range of about 1000 psia (6890 kPa) to about 2000 psia (13790 kPa).

In general, the hydrogenation reaction can be conducted in a batch, semi-batch, or continuous reactor design using fixed bed reactors, trickle bed reactors, slurry phase reactors, moving bed reactors, or any other design that allows for heterogeneous catalytic reactions. Examples of reactors can be seen in *Chemical Process Equipment—Selection and Design,* Couper et al., Elsevier 1990, which is incorporated herein by reference. It should be understood that the furanic substrate, hydrogen, any solvent, and the hydrodeoxygenation catalyst may be introduced into a suitable reactor separately or in various combinations.

Catalysts suitable for the hydrogenation reaction (hydrogenation catalysts) include heterogeneous catalysts, including solid-phase catalysts comprising one or more supported or unsupported metals. Suitable catalysts are disclosed in "Catalytic Hydrogenation and Dehydrogenation," *Fine Chemicals Through Heterogeneous Catalysis,* 2nd ed., Sheldon and van Bekkum, p. 351 and *Handbook of Heterogeneous Catalytic Hydrogenation for Organic Synthesis,* Nishimura 2001 Wiley, New York. In various embodiments, metal is present at a surface of a support (i.e., at one or more surfaces, external or internal). Typically, metal comprises at least one d-block metal (i.e., transition metal; groups 3-12 of the periodic table). In more preferred embodiments, the metal is selected from the group consisting of palladium, platinum, rhodium, ruthenium, nickel, cobalt, iron and combinations thereof. Additional other metals may be present, including one or more d-block metals, alone or in combination with one or more rare earth metals (e.g. lanthanides), alone or in combination with one or more main group metals (e.g. Al, Ga, Tl, In, Sn, Pb or Bi). In general, the metals may be present in various forms (e.g., elemental, metal oxide, metal hydroxides, metal ions, etc.). Typically, the metal(s) at a surface of a support may constitute from about 0.25% to about 10%, or from about 1% to about 8%, or from about 2.5% to about 7.5% (e.g., 5%) of the total weight of the catalyst.

In various embodiments, the hydrogenation catalyst comprises a first metal (M1) and a second metal (M2) at a surface of a support, wherein the M1 metal is selected from the group consisting of ruthenium, rhodium palladium, platinum, nickel, cobalt and iron and the M2 metal is selected from the group consisting of d-block metals, rare earth metals, and main group metals, wherein the M1 metal is not the same metal as the M2 metal. In various embodiments, M2 is selected from the group consisting of molybdenum, ruthenium, rhodium, palladium, iridium, platinum and gold. In various preferred embodiments, the M1 metal is palladium and the M2 metal is selected from the group consisting of manganese, iron, and cobalt.

The M1:M2 molar ratio may vary, for example, from about 500:1 to about 1:1, from about 250:1 to about 1:1, from about 100:1 to about 1:1, from about 50:1 to about 1:1, from about 20:1 to about 1:1, or from about 10:1 to about 1:1. In various other embodiments, the M1:M2 molar ratio may vary, for example, from about 1:100 to about 1:1, from about 1:50 to about 1:1, from about 1:10 to about 1:1, from about 1:5 to about 1:1, or from about 1:2 to about 1:1.

Moreover, the weight percents of M1 and M2 relative to the catalyst weight may vary. Typically, the weight percent of M1 may range from about 0.5% to about 10%, more preferably from about 1% to about 8%, and still more preferably from about 2.5% to about 7.5% (e.g., about 5%). The weight percent of M2 may range from about 0.25% to about 10%, from about 0.5% to about 8%, or from about 0.5% to about 5%.

In various other embodiments, a third metal (M3) may be added to produce a M1/M2/M3 catalyst wherein the M3 metal is not the same metal as the M1 metal and the M2 metal. In yet other embodiments a fourth metal (M4) may be added to produce a M1/M2/M3/M4 catalyst wherein the M4 metal is not the same metal as the M1 metal, the M2 metal or the M3 metal. M3 and M4 may each be selected from the group consisting of d-block metals, rare earth metals (e.g. lanthanides), or main group metals (e.g. Al, Ga, Tl, In, Sn, Pb or Bi).

Suitable catalyst supports include carbon, alumina, silica, ceria, titania, zirconia, niobia, zeolite, magnesia, clays, iron oxide, silicon carbide, aluminosilicates, and modifications, mixtures or combinations thereof. The support materials may be modified using methods known in the art such as heat treatment, acid treatment or by the introduction of a dopant (for example, metal-doped titanias, metal-doped zirconias (e.g., tungstated-zirconia), metal-doped cerias, and metal-modified niobias). Particularly preferred supports are carbon (which may be activated carbon, carbon black, coke or charcoal), alumina, zirconia, titania, zeolite and silica. In various embodiments, the support of the oxidation catalyst is selected from the group consisting of carbon, zirconia, zeolite, and silica.

When a catalyst support is used, the metals may be deposited using procedures known in the art including, but not limited to incipient wetness, ion-exchange, deposition-precipitation, and vacuum impregnation. When two or more metals are deposited on the same support, they may be deposited sequentially or simultaneously. In various embodiments, following metal deposition, the catalyst is dried at a temperature of at least about 50° C., more typically at least about 120° C. for a period of time of at least about 1 hour, more typically 3 hours or more. In these and other embodiments, the catalyst is dried under sub-atmospheric pressure conditions. In various embodiments, the catalyst is reduced after drying (e.g., by flowing 5% $H_2$ in $N_2$ at 350° C. for 3 hours). Still further, in these and other embodiments, the catalyst is calcined, for example, at a temperature of at least about 500° C. for a period of time (e.g., at least about 3 hours).

The hydrogenation reaction is preferably conducted in the substantial absence of added halogen. It is currently believed that the introduction of a source of halogen independent of that which, if any, is within the furanic substrate inhibits the conversion rate and selectivity of the reaction to tetrahydrofuranic substrate.

The reaction product of the hydrogenation step is a tetrahydrofuranic substrate, which substrate is unexpectedly convertible to an adipic acid product in high yield. The tetrahydrofuranic substrate of the present invention is set forth in formula III, below (and further includes salts thereof):

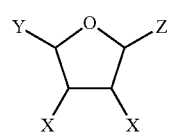

III wherein each X is independently selected from the group consisting of —OH, —OR$^2$, and —H, or, in some embodiments, X is independently selected from the group consisting of —OH and —H, or, in some embodiments, each X is —OH, or, in some embodiments, each X is —H; Y is selected from the group consisting of —C(O)OH, —C(O)OR$^1$, —C(O)NR$^3$R$^4$, and —CH$_2$NR$^3$R$^4$; Z is selected from the group consisting of —C(O)OH, —C(O)OR$^1$, —C(O)NR$^3$R$^4$, and —CH$_2$NR$^3$R$^4$; each R$^1$ is independently selected from the group consisting of hydrocarbyl, and substituted hydrocarbyl; each R$^2$ is independently selected from the group consisting of hydrocarbyl and substituted hydrocarbyl; each R$^3$ is independently selected from the group consisting of hydrogen, hydrocarbyl, and substituted hydrocarbyl; each R$^4$ is independently selected from the group consisting of hydrogen, hydrocarbyl, and substituted hydrocarbyl; and, preferably, each hydrocarbyl or substituted hydrocarbyl in any of the aforementioned $R^1$, $R^2$, $R^3$, and/or $R^4$ can be independently selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl and heteroarylalkyl, in each case optionally substituted. If substituted, the aforementioned $R^1$, $R^2$, $R^3$, and/or $R^4$ can be preferably substituted with one or more of $C_1$-$C_4$ alkyl, hydroxyl, amine, $C_1$-$C_4$ alkylamino, thiol, and $C_1$-$C_4$ thioalkyl.

As used throughout this disclosure, the term "hydrocarbyl" refers to hydrocarbyl moieties, preferably containing 1 to about 50 carbon atoms, preferably 1 to about 30 carbon atoms, and even more preferably 1 to about 18 carbon atoms, including branched or unbranched, and saturated or unsaturated species. Preferred hydrocarbyl can be selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl, heteroarylalkyl, and the like. A hydrocarbyl may be optionally substituted hydrocarbyl. Hence, various hydrocarbyls can be further selected from substituted alkyl, substituted cycloalkyl and the like.

III. Conversion of Tetrahydrofuranic Substrate to Adipic Acid Product

In accordance with the present invention, an adipic acid product is produced by processes comprising the step of hydrodeoxygenating a tetrahydrofuranic substrate by reacting the same with hydrogen in the presence of a hydrodeoxygenation catalyst (i.e., catalyst suitable for the step of hydrodeoxygenation), an added source of halogen and a solvent, to convert at least a portion of the tetrahydrofuranic substrate to an adipic acid product.

In various embodiments, the tetrahydrofuranic substrate comprises THFDCA, and a portion of the acid is converted by hydrodeoxygenation to an adipic acid product comprising adipic acid.

Without being bound by theory, it is believed that during this reaction THFDCA is ring opened and halogenated in the presence of the halogen source to produce a ring opened halogenated intermediate containing a carbon-halogen bond The carbon-halogen bond of the halogenated intermediate is believed to be converted to a carbon-hydrogen bond via one or more of the following pathways. In a first pathway, the halogenated intermediate reacts with hydrogen in the presence of the hydrodeoxygenation catalyst leading to the formation of a carbon-hydrogen bond along with the generation of hydrohalic acid. In a second pathway, the halogenated intermediate undergoes a dehydrohalogenation reaction to form an olefin intermediate and hydrohalic acid. The olefin is further reduced in the presence of the hydrodeoxygenation catalyst leading to the formation of a carbon-hydrogen bond. Effecting the reaction pursuant to the above described first and second pathways generates hydrohalic acid as a by-product, which is available for further reaction. In a third pathway, the halogenated intermediate reacts with hydrohalic acid leading to the formation of a carbon-hydrogen bond along with the formation of molecular halogen (or interhalogen). Effecting the reaction pursuant to the third pathway generates molecular halogen as a by-product, which is available for further reaction. One or more of the various pathways described above may occur concurrently.

The halogen source may be in a form selected from the group consisting of atomic, ionic, molecular and mixtures thereof. In various embodiments, the halogen source is hydrohalic acid. Preferred halogen sources include HBr and HI and mixtures thereof. Unexpectedly, HI has enabled the conversion of greater than 90% of THFDCA to adipic acid product.

Generally, the molar ratio of halogen source to the tetrahydrofuranic substrate is equal to or less than about 1. Typically, the mole ratio of the halogen source to the substrate is from about 0.9:1 to about 0.1:1, more typically from about 0.7:1 to about 0.3:1, and still more typically about 0.5:1.

Generally, the reaction allows for recovery of the halogen source and catalytic quantities (where molar ratio of halogen to the hydrodeoxygenation substrate is less than about 1) of halogen can be used, recovered and recycled for continued use as a halogen source.

Generally, the temperature of the hydrodeoxygenation reaction of the furanic substrate is at least about 20° C., typically at least about 80° C., and more typically at least about 100° C. In various embodiments, the temperature of the hydrodeoxygenation reaction is conducted in the range of from about 20° C. to about 250° C., from about 80° C. to about 200° C., more preferably from about 120° C. to about 180° C., and still more preferably from about 140° C. to about 180° C.

Typically, in the hydrodeoxygenation reaction, the partial pressure of hydrogen is at least about 25 psia (172 kPa), more typically at least about 200 psia (1379 kPa) or at least about 400 psia (2758 kPa). In various embodiments, the partial pressure of hydrogen is from about 25 psia (172 kPa) to about 2500 psia (17237 kPa), from about 200 psia (1379 kPa) to about 2000 psia (13790 kPa), or from about 400 psia (2758 kPa) to about 1500 psia (10343 kPa).

The hydrodeoxygenation reaction is typically conducted in the presence of a solvent. Solvents suitable for the selective hydrodeoxygenation reaction include water and carboxylic acids, amides, esters, lactones, sulfoxides, sulfones and mixtures thereof. Preferred solvents include water, mixtures of water and weak carboxylic acid, and weak carboxylic acid. A preferred weak carboxylic acid is acetic acid.

Hydrodeoxygenation of the tetrahydrofuranic substrate can be conducted in a batch, semi-batch, or continuous reactor design using fixed bed reactors, trickle bed reactors, slurry phase reactors, moving bed reactors, or any other design that allows for heterogeneous catalytic reactions. Examples of reactors can be seen in Chemical Process Equipment—Selection and Design, Couper et al., Elsevier 1990, which is incorporated herein by reference. It should be understood that the hydrodeoxygenation substrate, halogen source, hydrogen, any solvent, and the hydrodeoxygenation catalyst may be introduced into a suitable reactor separately or in various combinations.

In various embodiments, the hydrogenation and hydrodeoxygenation reactions can be conducted in the same reactor, particularly when the solvent for each reaction is the same and a catalyst effective both as a catalyst for hydrogenation and hydrodeoxygenation reactions is employed. In such embodiments, it will be apparent to those skilled in the art that many of the reactors above disclosed are typically capable of being operated under a variety of conditions and can be readily controlled in order to optimize reaction conditions for the desired conversion of reactants. Methods for determining optimized conversion conditions can include, for example, periodic sampling of the reaction mixture via known reactor off-take mechanisms, analysis of the sampled product and control of the process conditions in response thereto. Further, in such embodiments, the source of halogen is, most preferably, added to the reactor after the hydrogenation reaction has been conducted under process conditions sufficient to convert a suitable portion of the furanic substrate to the tetrahydrofuranic substrate.

In more preferred embodiments, the hydrogenation and hydrodeoxygenation reactions can be conducted in separate reactors, wherein the solvent for each reaction is the same and the product from the hydrogenation reaction is passed directly into the hydrodeoxygenation reactor. In such embodiments, it will be apparent to those skilled in the art that many of the reactors above disclosed are typically capable of being operated under a variety of conditions and can be readily controlled in order to optimize reaction conditions for the desired conversion of reactants.

In more preferred embodiments, the hydrodeoxygenation catalysts are heterogeneous, but a suitable homogeneous catalyst may be employed. In these and various other preferred embodiments, the hydrodeoxygenation catalyst comprises a solid-phase heterogeneous catalyst in which one or more metals is present at a surface of a support (i.e., at one or more surfaces, external or internal). Preferred metals are d-block metals which may be used alone, in combination with each other, in combination with one or more rare earth metals (e.g. lanthanides), and in combination with one or more main group metals (e.g., Al, Ga, Tl, In, Sn, Pb or Bi). Preferred d-block metals are selected from the group consisting of cobalt, nickel, ruthenium, rhodium, palladium, osmium, iridium, platinum and combinations thereof. More preferred d-block metals are selected from the group consisting of ruthenium, rhodium, palladium, platinum, and combinations thereof. In general, the metals may be present in various forms (e.g., elemental, metal oxide, metal hydroxides, metal ions etc.). Typically, the metal(s) at a surface of a support may constitute from about 0.25% to about 10%, or from about 1% to about 8%, or from about 2.5% to about 7.5% (e.g., 5%) of the catalyst weight.

In various embodiments, the hydrodeoxygenation catalyst comprises two or more metals. For example, two of more metals (M1 and M2) may be co-supported on or within the same support (e.g., as a mixed-metal catalyst on silica; M1/M2/Silica catalyst), or they may be supported on different support materials. In various embodiments the hydrodeoxygenation catalyst comprises a first metal (M1) and a second metal (M2) at a surface of a support, wherein the M1 metal comprises a d-block metal and the M2 metal is selected from the group consisting of d-block metals, rare earth metals, and main group metals, wherein the M1 metal is not the same metal as the M2 metal. In various embodiments, the M1 metal is selected from the group consisting of cobalt, nickel, ruthenium, rhodium, palladium, osmium, iridium, and platinum. In more preferred embodiments, the M1 metal is selected from the group consisting of ruthenium, rhodium, palladium, and platinum. In various embodiments, the M2 metal is selected from the group consisting of titanium, vanadium, chromium, manganese, iron, cobalt, nickel, copper, molybdenum, ruthenium, rhodium, palladium, silver, tungsten, iridium, platinum, and gold. In more preferred embodiments, the M2 metal is selected from the group consisting of molybdenum, ruthenium, rhodium, palladium, iridium, platinum, and gold.

In more preferred embodiments, the M1 metal of the hydrodeoxygenation catalyst is selected from the group of platinum, rhodium and palladium, and the M2 metal is selected from the group consisting of ruthenium, rhodium, palladium, platinum, and gold.

In various embodiments, the M1:M2 molar ratio of the hydrodeoxygenation catalyst may vary, for example, from about 500:1 to about 1:1, from about 250:1 to about 1:1, from about 100:1 to about 1:1, from about 50:1 to about 1:1, from about 20:1 to about 1:1, or from about 10:1 to about 1:1. In various other embodiments, the M1:M2 molar ratio may vary, for example, from about 1:100 to about 1:1, from about 1:50 to about 1:1, from about 1:10 to about 1:1, from about 1:5 to about 1:1, or from about 1:2 to about 1:1.

Moreover, in various embodiments, the weight percents of M1 and M2 of the hydrodeoxygenation catalyst relative to the total catalyst weight may vary. Typically, the weight percent of M1 may range from about 0.5% to about 10%, more preferably from about 1% to about 8%, and still more preferably from about 2.5% to about 7.5% (e.g., about 5%). The weight percent of M2 may range from about 0.25% to about 10%, from about 0.5% to about 8%, or from about 0.5% to about 5%.

In various other embodiments, a third metal (M3) may be added to produce a M1/M2/M3 hydrodeoxygenation catalyst wherein the M3 metal is not the same metal as the M1 metal and the M2 metal. In other embodiments a fourth metal (M4) may be added to produce a M1/M2/M3/M4 hydrodeoxygenation catalyst wherein the M4 metal is not the same metal as the M1 metal, the M2 metal or the M3 metal. M3 and M4 may each be selected from the group consisting of d-block metals, rare earth metals (e.g. lanthanides), or main group metals (e.g. Al, Ga, Tl, In, Sn, Pb or Bi).

Preferred hydrodeoxygenation catalyst supports include carbon, alumina, silica, ceria, titania, zirconia, niobia, zeolite, magnesia, clays, iron oxide, silicon carbide, aluminosilicates, and modifications, mixtures or combinations thereof. The supports may be modified through methods known in the art such as heat treatment, acid treatment, the introduction of a dopant (for example, metal-doped titanias, metal-doped zirconias (e.g. tungstated zirconia), metal-doped cerias, and metal-modified niobias). In various preferred embodiments, the hydrodeoxygenation catalyst support is selected from the group consisting of carbon, silica, zirconia and titania.

When a catalyst support is used for the hydrodeoxygenation catalyst, the metals may be deposited using procedures known in the art including, but not limited to incipient wetness, ion-exchange, deposition-precipitation and vacuum impregnation. When the two or more metals are deposited on the same support, they may be deposited sequentially, or simultaneously. In various embodiments, following metal deposition, the hydrodeoxygenation catalyst is dried at a temperature of at least about 50° C., more typically at least about 120° C. or more for a period of time of at least about 1 hour, more typically at least about 3 hours or more. In these and other embodiments, the catalyst is dried under sub-atmospheric conditions. In various embodiments, the hydrodeoxygenation catalyst is reduced after drying (e.g., by flowing 5% $H_2$ in $N_2$ at 350° C. for 3 hours). Still further, in these and other embodiments, the hydrodeoxygenation catalyst is calcined, for example, at a temperature of at least about 500° C. for a period of time (e.g., at least about 3 hours).

As should be apparent from the disclosure herein, in certain preferred embodiments, the hydrodeoxygenation catalysts useful for the hydrodeoxygenation of the tetrahydrofuranic substrate are also effective as catalysts for the hydrogenation of the furanic substrate.

Without being bound by theory not expressly recited in the claims, catalysts mixtures (co-catalysts or mixed metal catalysts) containing more than one metal may affect separate steps of the mechanistic reaction pathway.

Surprisingly, the production of adipic acid product from the tetrahydrofuranic substrate is quite facile. Yields of adipic acid product from the hydrodeoxygenation of this substrate can be at least about 90%, or more.

Adipic acid product produced in accordance with the processes of the present invention may be recovered from the hydrodeoxygenation reaction by, for example, one or more combinations of conventional methods known in the art such as, for example, separation of the reaction liquids from catalyst (typically a solid) and the halogen (as, for example, vapor phase separation thereof), followed by solvent extraction/evaporation or adipic acid product crystallization.

IV. Downstream Chemical Products

Various methods are known in the art for conversion of adipic acid to downstream chemical products or intermediates including adipate esters, polyesters, adiponitrile, hexamethylene diamine (HMDA), caprolactam, caprolactone, 1,6-hexanediol, aminocaproic acid, and polyamide such as nylons. For conversions from adipic acid, see for example, without limitation, U.S. Pat. Nos. 3,671,566, 3,917,707, 4,767,856, 5,900,511, 5,986,127, 6,008,418, 6,087,296, 6,147,208, 6,462,220, 6,521,779, 6,569,802, and Musser, "Adipic Acid" in *Ullmann's Encyclopedia of Industrial Chemistry, Wiley-VCH*, Weinheim, 2005.

In accordance with one aspect of the invention, when acetic acid is employed as a solvent in at least the hydrodeoxygenation of the tetrahydrofuranic substrate, the adipic acid product resulting therefrom will comprise at least one acyl-group-containing compound and, possibly, one or more diacyl compounds; i.e., when Y or $Z=-CH_2NR^3R^4$ wherein $R^3$ and $R^4$ is H, then one or more H atoms will likely be converted to $-C(O)Me$ (acyl group), for example N,N'-diacetyl hexamethylenediamine. In such aspect of the invention, the acyl group(s) of such compounds can readily be hydrolyzed (for example, in the presence of a base), wherein they are reconverted to an —H, and the acetic acid can then be regenerated. Thus, hexamethylenediamine (HDMA) can be produced.

In various embodiments, an adipic acid product is converted to adiponitrile wherein the adipic acid product is prepared in accordance with the present invention. Adiponitrile can be used industrially for the manufacture of hexamethylenediamine, see Smiley, "Hexamethylenediamine" in Ullmann's Encyclopedia of Industrial Chemistry, Wiley-VCH 2009. Therefore, in further embodiments, an adipic acid product is converted to hexamethylenediamine wherein the adipic acid product is prepared in accordance with the present invention.

Adipic acid is useful in the production of polyamides, such as nylon 6,6 and nylon 4,6. See, for example, U.S. Pat. No. 4,722,997, and Musser, "Adipic Acid" in *Ullmann's Encyclopedia of Industrial Chemistry*, Wiley-VCH, Weinheim, 2005. The hexamethylenediamine formed from an adipic acid product prepared in accordance with the present invention can likewise be further used for the preparation of polyamides such as nylon 6,6 and nylon 6,12. See, for example Kohan, Mestemacher, Pagilagan, Redmond, "Polyamides" in *Ullmann's Encyclopedia of Industrial Chemistry*, Wiley-VCH, Weinheim, 2005.

Accordingly, adipic acid and a polymer precursor derived from an adipic acid product (e.g., hexamethylenediamine) may be reacted to produce a polyamide, wherein the adipic acid product is prepared in accordance with the present invention. Polymer precursor, as used herein, refers to a monomer which can be converted to a polymer (or copolymer) under appropriate polymerization conditions. In various embodiments, the polyamide comprises nylon 6,6. In these embodiments, nylon 6,6 is produced by reacting an adipic acid product with a polymer precursor derived from an adipic acid product, wherein the polymer precursor comprises hexamethylenediamine. In these embodiments, hexamethylenediamine may be prepared by converting an adipic acid product to adiponitrile which then may be converted to hexamethylene diamine, wherein the adipic acid product is prepared in accordance with the present invention.

In other embodiments, an adipic acid product is converted to caprolactam wherein the adipic acid product is prepared in accordance with the present invention. The caprolactam formed can be further used for the preparation of polyamides by means generally known in the art. Specifically, caprolactam can be further used for the preparation of nylon 6. See, for example Kohan, Mestemacher, Pagilagan, Redmond, "Polyamides" in *Ullmann's Encyclopedia of Industrial Chemistry*, Wiley-VCH, Weinheim, 2005.

In various embodiments, nylon 6 is produced by reacting caprolactam derived from an adipic acid product prepared in accordance with the present invention.

In other embodiments, adipic acid and a polymer precursor may be reacted to produce a polyester, wherein the adipic acid product is prepared in accordance with the present invention.

In other embodiments, an adipic acid product is converted to 1,6-hexanediol wherein the adipic acid product is prepared in accordance with the present invention. 1,6-hexanediol is a valuable chemical intermediate used in the production of polyesters and polyurethanes. Accordingly, in various embodiments, polyester may be prepared by reacting adipic acid and 1,6-hexandiol derived from an adipic acid product, prepared in accordance with the present invention.

In various embodiments a salt of adipic acid may be produce wherein the process comprises reacting adipic acid with hexamethylenediamine, thereby forming the salt, wherein adipic acid is prepared in accordance with the present invention.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

EXAMPLES

The following non-limiting examples are provided to further illustrate the present invention.

Reactions were conducted in 1 mL glass vials housed in a pressurized vessel in accordance with the procedures described in the examples below. Product yields were determined using mass spectrometry through comparison with calibration standards.

Preparation of M1/Silica Catalysts (M1=Rh, Pd, Pt)

2 g of dried 5 µm Silica Cariact (Fuji Silysia) was weighed into vials. Suitably concentrated M1 stock solutions (M1=Rh, Pd, Pt) were prepared from concentrated acidic stock solutions purchased from Heraeus (see Table 1). For each M1, multiple additions of the dilute M1 stock solution were added to the silica (silica pore volume=0.7 mL/g) until a total volume of 1.4 ml was reached. After each addition, the mixtures were agitated to impregnate the silica. Post impregnation, the M1/Silica mixtures were dried in a furnace at 120° C. for 12 hours, followed by calcination at 500° C. for 3 hours. Upon cooling the catalysts were stored in a dessicator until used.

Preparation of Tetrahydrofuran-2,5-Dicarboxylic Acid (THFDCA)

A 100 mL pressure vessel with a glass liner and an impeller was charged with 1.87 g of furan-2,5-dicarboxylic acid, 0.5 g of 4% Pd/Silica and 40 mL of acetic acid. The pressure vessel was purged 3 times with nitrogen, and 2 times with hydrogen. The vessel was then pressurized to 750 psig hydrogen and heated to 140° C. for 3 hours. After cooling the vessel was vented and the solids were separated by filtration. The acetic acid solution was evaporated under vacuum to provide 1.68 g (88% yield) of tetrahydrofuran-2,5-dicarboxylic acid.

Tetrahydrofuran-2,5-Dicarboxilic Acid to Adipic Acid Reactions

M1/Silica catalysts were transferred to 1 mL glass vials within a 96-well reactor insert (Symyx Solutions). Each vial within each array received a glass bead and 250 μL of 0.2 M THFDCA, 0.1 to 0.3 M of HBr (Sigma-Aldrich) in Acetic Acid (Sigma-Aldrich), or HI (Sigma-Aldrich). Upon solution addition, the arrays of vials were covered with a Teflon pinhole sheet, a silicone pin-hole mat and steel gas diffusion plate (Symyx Solutions). The reactor insert was placed in a pressure vessel, pressurized and vented 3 times with nitrogen and 3 times with hydrogen before being pressurized with hydrogen to 710 psig, heated to 140° C. or 160° C. and shaken for 3 hours. After 3 hours the reactors were cooled, vented and purged with nitrogen. 750 μl of water was then added to each vial. Following the water addition, the arrays were covered and shaken to ensure adequate mixing. Subsequently, the covered arrays were placed in a centrifuge to separate the catalyst particles. Each reaction samples was then diluted 100-fold with water to generate a sample for analysis by mass spectrometry. The results are presented in Table 1.

TABLE 1

| Example Number | Catalyst (wt. % M1/Support) | M1 Precursor | Halide Source | Halide Concentration (M) | Temp (° C.) | Catalyst Amount (mg) | Adipic Acid Yield (%) |
|---|---|---|---|---|---|---|---|
| 1 | 5% Pd/Silica 5 μm Cariact | $Pd(NO_3)_2$ | HI | 0.2 | 160 | 8 | 99 |
| 2 | 5% Rh/Silica 5 μm Cariact | $Rh(NO_3)_3$ | HI | 0.2 | 160 | 8 | 91 |
| 3 | 5% Pd/Silica 5 μm Cariact | $Pd(NO_3)_2$ | HI | 0.2 | 140 | 8 | 70 |
| 4 | 5% Rh/Silica 5 μm Cariact | $Rh(NO_3)_3$ | HI | 0.2 | 140 | 8 | 68 |
| 5 | 5% Pd/Silica 5 μm Cariact | $Pd(NO_3)_2$ | HI | 0.1 | 160 | 8 | 49 |
| 6 | 5% Rh/Silica 5 μm Cariact | $Rh(NO_3)_3$ | HI | 0.1 | 160 | 8 | 33 |

What is claimed is:

1. A process for preparing an adipic acid product comprising reacting a tetrahydrofuranic substrate with hydrogen, in the presence of a hydrodeoxygenation catalyst, a solvent and a source of halogen, to convert at least a portion of the tetrahydrofuranic substrate to the adipic acid product, wherein the tetrahydrofuranic substrate comprises a compound of formula III

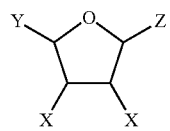

III or salt thereof, and the adipic acid product comprises a compound of formula II

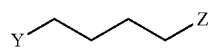

II where each X is independently selected from the group consisting of —OH, —OR², and —H;

Y is selected from the group consisting of —C(O)OH, —C(O)OR¹, —C(O)NR³R⁴, and —CH₂N R³R⁴;

Z is selected from the group consisting of —C(O)OH, —C(O)OR¹, —C(O)NR³R⁴, and —CH₂N R³R⁴;

each R¹ is independently selected from the group consisting of hydrocarbyl and substituted hydrocarbyl;

each R² is independently selected from the group consisting of hydrocarbyl and substituted hydrocarbyl;

each R³ is independently selected from the group consisting of hydrogen, hydrocarbyl, and substituted hydrocarbyl; and each R⁴ is independently selected from the group consisting of hydrogen, hydrocarbyl, and substituted hydrocarbyl.

2. The process as set forth in claim 1 wherein the source of halogen comprises hydrogen bromide or hydrogen iodide.

3. The process as set forth in claim 1 further comprising reacting a furanic substrate with hydrogen, in the presence of a hydrogenation catalyst and a solvent, but in the absence of an added source of halogen, to produce the tetrahydrofuranic substrate, wherein the furanic substrate comprises a compound of formula I

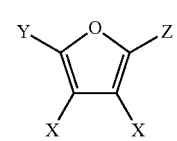

I or a salt thereof, or an intermolecular homomer or heteromer thereof, or intermolecular or intramolecular anhydrides or stereoisomers thereof, where each X, Y, and Z are as defined for formula III.

4. The process as set forth in claim 3 wherein the solvent comprises acetic acid.

5. The process as set forth in claim 1 wherein the solvent comprises a weak carboxylic acid.

6. The process as set forth in claim 1 wherein at least a portion of the tetrahydrofuranic substrate is derived from a carbohydrate source.

7. The process as set forth in claim 1 wherein the hydrodeoxygenation catalyst comprises a heterogeneous catalyst.

8. The process as set forth in claim 7 wherein the hydrodeoxygenation catalyst comprises at least one d-block metal at a surface of a support.

9. The process as set forth in claim 8 wherein the d-block metal is selected from the group consisting of Ru, Rh, Pd, Pt, and combinations thereof.

10. The process as set forth in claim 1 wherein the hydrodeoxygenation catalyst comprises a first metal and a second metal, wherein the first metal is selected from the group consisting of Ru, Rh, Pd and Pt and the second metal is selected from the group consisting of Mo, Ru, Rh, Pd, Ir, Pt, and Au, and wherein the second metal is not the same as the first metal.

11. The process as set forth in claim 3 wherein the hydrodeoxygenation catalyst support comprises a material selected from the group consisting of carbon, silica, zirconia, and titania.

12. The process as set forth in claim 1 wherein the molar ratio of the source of halogen to the tetrahydrofuranic substrate is equal to or less than about 1.

13. The process as set forth in claim 3 wherein the temperature of the hydrogenation reaction mixture is from about 60° C. to about 200° C.

14. The process as set forth in claim 3 wherein the hydrodeoxygenation reaction is conducted under a partial pressure of hydrogen ranging from about 25 psia (172 kPa) to about 2500 psia (17237 kPa).

15. The process as set forth in claim 3 wherein at least a portion of the furanic substrate is derived from a carbohydrate source.

16. The process as set forth in claim 3 wherein the hydrogenation catalyst comprises a heterogeneous catalyst comprising at least one d-block metal at a surface of a support.

17. The process as set forth in claim 16 wherein the d-block metal is selected from the group consisting of Ru, Rh, Pd, Pt, Ni, Co, Fe and combinations thereof.

18. The process as set forth in claim 3 wherein the hydrogenation catalyst comprises a first metal and a second metal, wherein the first metal is selected from the group consisting of Ru, Rh, Pd, Pt, Ni, Co and Fe, and the second metal is selected from the group consisting of Mo, Ru, Rh, Pd, Ir, Pt, and Au, and wherein the second metal is not the same as the first metal.

19. The process as set forth in 17 wherein the hydrogenation catalyst support is selected from the group consisting of carbon, zirconia, zeolite and silica.

20. The process of claim 1 wherein the yield of adipic acid product is at least about 90%.

* * * * *